(12) United States Patent
Jones

(10) Patent No.: US 9,533,100 B2
(45) Date of Patent: Jan. 3, 2017

(54) DOSE SETTING MECHANISM FOR PRIMING A DRUG DELIVERY DEVICE

(75) Inventor: Christopher Jones, Tewkesbury (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 731 days.

(21) Appl. No.: 13/322,758

(22) PCT Filed: May 28, 2010

(86) PCT No.: PCT/EP2010/057485
§ 371 (c)(1),
(2), (4) Date: Mar. 15, 2012

(87) PCT Pub. No.: WO2010/139639
PCT Pub. Date: Dec. 9, 2010

(65) Prior Publication Data
US 2012/0165743 A1    Jun. 28, 2012

Related U.S. Application Data

(60) Provisional application No. 61/182,841, filed on Jun. 1, 2009.

(30) Foreign Application Priority Data

Jul. 10, 2009    (EP) .................................... 09009048

(51) Int. Cl.
*A61M 5/31*    (2006.01)
*A61M 5/24*    (2006.01)
*A61M 5/315*    (2006.01)

(52) U.S. Cl.
CPC ............. *A61M 5/24* (2013.01); *A61M 5/3146* (2013.01); *A61M 5/31511* (2013.01);
(Continued)

(58) Field of Classification Search
CPC ..................... A61M 5/31553; A61M 5/31555; A61M 5/3155; A61M 5/31548; A61M 5/31545; A61M 5/31595; A61M 5/31591; A61M 5/31538; A61M 5/31536; A61M 5/31551; A61M 5/31535; A61M 5/31541; A61M 2005/3154
See application file for complete search history.

(56) References Cited

U.S. PATENT DOCUMENTS 3,302,462 A    2/1967   Pursell
5,514,097 A    5/1996   Knauer
(Continued)

FOREIGN PATENT DOCUMENTS

CN    1901056 A    1/2007
DE    9301334.5    4/1993
(Continued)

OTHER PUBLICATIONS

Text of the First Office Action for Chinese Patent Application No. 201080032171.2.
(Continued)

*Primary Examiner* — Nathan R Price
*Assistant Examiner* — Anh Bui
(74) *Attorney, Agent, or Firm* — McDonnell Boehnen Hulbert & Berghoff LLP

(57) ABSTRACT

A method and system for priming a drug delivery device are provided. The drug delivery device includes a forced priming feature that requires the user to move the dose dial sleeve (3) axially to cause the spindle (5) to pre-load a cartridge bung before a first dose can be dialed.

10 Claims, 2 Drawing Sheets

(52) U.S. Cl.
CPC .... *A61M 5/31535* (2013.01); *A61M 5/31551* (2013.01); *A61M 5/31561* (2013.01); *A61M 5/31585* (2013.01); *A61M 2005/2407* (2013.01); *A61M 2005/2488* (2013.01); *A61M 2005/2492* (2013.01); *A61M 2005/3104* (2013.01); *A61M 2005/3125* (2013.01)

(56) References Cited

U.S. PATENT DOCUMENTS

| | | | |
|---|---|---|---|
| 5,584,815 | A | 12/1996 | Pawelka et al. |
| 5,591,136 | A | 1/1997 | Gabriel |
| 5,792,117 | A | 8/1998 | Brown |
| 6,090,080 | A | 7/2000 | Jost et al. |
| 6,936,032 | B1 | 8/2005 | Bush, Jr. et al. |
| 2004/0127858 | A1* | 7/2004 | Bendek et al. ............... 604/208 |
| 2004/0162528 | A1 | 8/2004 | Horvath et al. |
| 2004/0186437 | A1 | 9/2004 | Frenette et al. |
| 2004/0210199 | A1 | 10/2004 | Atterbury et al. |
| 2004/0236285 | A1 | 11/2004 | Fisher et al. |
| 2005/0137571 | A1 | 6/2005 | Hommann |
| 2005/0177115 | A1 | 8/2005 | Broennimann et al. |
| 2005/0261634 | A1* | 11/2005 | Karlsson ...................... 604/197 |
| 2006/0153693 | A1 | 7/2006 | Fiechter et al. |
| 2006/0178630 | A1* | 8/2006 | Bostrom et al. ............. 604/135 |
| 2006/0258988 | A1 | 11/2006 | Keitel et al. |
| 2006/0270985 | A1* | 11/2006 | Hommann .......... A61M 5/2033 604/136 |
| 2007/0016142 | A1* | 1/2007 | Burren et al. ................ 604/207 |
| 2007/0021718 | A1 | 1/2007 | Burren et al. |
| 2008/0027397 | A1 | 1/2008 | DeRuntz et al. |
| 2008/0077095 | A1 | 3/2008 | Kirchhofer |
| 2008/0208123 | A1 | 8/2008 | Hommann |
| 2009/0227959 | A1 | 9/2009 | Hirschel et al. |
| 2009/0254044 | A1* | 10/2009 | Kohlbrenner et al. ....... 604/207 |
| 2010/0331789 | A1* | 12/2010 | Jones ............................ 604/207 |

FOREIGN PATENT DOCUMENTS

| | | |
|---|---|---|
| DE | 19730999 C1 | 12/1998 |
| DE | 29818721 U1 | 3/2000 |
| DE | 102005063311 A1 | 8/2006 |
| DE | 102005060928 A1 | 6/2007 |
| DE | 102006038123 A1 | 2/2008 |
| DE | 102007026083 A1 | 11/2008 |
| EP | 0897728 A1 | 2/1999 |
| EP | 0937471 A2 | 8/1999 |
| EP | 0937482 A2 | 8/1999 |
| EP | 1541185 A1 | 6/2005 |
| GB | 2443390 A | 5/2008 |
| JP | 2008506418 A | 3/2008 |
| WO | 2005044346 A2 | 5/2005 |
| WO | 2006058883 A2 | 6/2006 |

OTHER PUBLICATIONS

Form PCT/IB1326, Notification Concerning Transmittal of International Preliminary Report on Patentability.
English Translation of Japanese Patent Application No. 2012-513568, Notice of Reasons for Rejection dated Mar. 28, 2014.

* cited by examiner

DOSE SETTING MECHANISM FOR PRIMING A DRUG DELIVERY DEVICE

CROSS REFERENCE TO RELATED APPLICATIONS

The present application is a 35 U.S.C. 371 National Application of PCT/EP2010/057485 filed May 28, 2010, which claims priority to U.S. Provisional Patent Application No. 61/182,841, filed Jun. 1, 2009 and European Patent Application No. 09009048.1 filed Jul. 10, 2009, the entire contents of which are incorporated entirely herein by reference.

BACKGROUND

Field of the Present Patent Application

The present patent application is generally directed to drug delivery devices. More particularly, the present patent application is generally directed to drug delivery devices, such as pen type drug delivery devices. Such devices provide for self administration of medicinal product from a multi-dose cartridge and permit a user to set the delivery dose. The present application may find application in both resettable (i.e., reusable) and non-resettable (i.e., non-reusable) type drug delivery devices. However, aspects of the invention may be equally applicable in other scenarios as well. Specifically, the invention is directed to a mechanism and method to require a user to prime the drug delivery device before the first injection.

Background

Pen type drug delivery devices have application where regular injection by persons without formal medical training occurs. This is increasingly common among patients having diabetes where self-treatment enables such patients to conduct effective management of their disease.

In certain types of medication delivery devices, such as pen type devices, cartridges of medication are used. These cartridges are housed in a cartridge holder or cartridge housing. Such cartridges include a bung or stopper at one end. At the other end of the cartridge, the cartridge comprises a pierceable seal. To dispense a dose of medication from such a cartridge, the medication delivery device has a dose setting mechanism that uses a spindle to move in a distal direction towards the cartridge and to press a distal end of the spindle against the bung. This expels a certain set dose of medication from the cartridge. In order to insure dose accuracy, it is important that the distal end of the spindle remain on the bung of the cartridge before, during and after injection of a dose of medicament.

One perceived disadvantage of certain know medication delivery devices is that because of the various tolerance differences that may occur during manufacturing (e.g., tolerance differences that may arise during component molding) of the various parts making up the drug delivery device and the desire to not pre-load the bung axially in the assembled device, there may be a gap between the end of the spindle and the cartridge bung when the medication delivery device is assembled. In other words, when initially assembled, the cartridge (and hence cartridge bung) may not be in contact with the distal end of the spindle. Therefore, if a user using the drug delivery device for the first time dials a dose, the actual dose received may be equal to the dialed dose less the initial gap between the distal end of the spindle and cartridge bung. The air gap between the cartridge bung and distal end of the spindle may be equivalent to a dose that causes the received dose that is outside preferred dose accuracy limits. For example, this air gap may be equivalent to the loss of between 0 and 10 units (i.e., 0-0.14 milliliters) of drug product on the first dose.

There is, therefore, a general need to take these perceived issues into consideration when designing either resettable or non-resettable drug delivery devices, such as pen type drug delivery devices. The invention solves the above-described problem by requiring the user to prime the injection device to close the gap by pre-loading the bung.

SUMMARY

It is an object of the present invention to provide a dose setting mechanism and a drug delivery device as well as a respective method allowing a priming step prior to the first use of the mechanism or device.

This object is solved by the dose setting mechanism of claim 1.

For a dose setting mechanism having a dose dial sleeve which travels on a helical path of a housing component, preferably an inner body or inner housing, during setting and/or administering of a drug, it is the main concept of the present invention to separate the dose dial sleeve from a threaded part which engages a thread on the housing component. In other words, an additional nut-like part is provided which engages the thread on the housing component and which allows an axial movement relative to the dose dial sleeve. This axial movement between the dose dial sleeve and the nut-like part effects priming of the device, i.e. it closes or reduces a possible gap which may or may not be present between the end of the spindle and the cartridge bung. Preferably, the additional nut-like part is coupled to the dose dial sleeve to prevent any relative rotational movement between these two parts but allowing said relative axial movement during priming.

According to an exemplary arrangement, a dose setting mechanism for a drug delivery device is provided. The drug delivery device includes a dose dial sleeve and a housing component, like an inner body (inner housing). The dose dial sleeve is coupled to a nut that is rotationally engaged to the inner body. In this exemplary arrangement, the dose dial sleeve moves axially in the distal direction during priming of the drug delivery device relative to the nut. Preferably, this forms an irreversible lock. Further, the dose dial sleeve rotates on a helical path during dose setting of the drug delivery device.

According to another arrangement, the invention relates to a drug delivery device having a forced priming feature comprising a cartridge holder containing a cartridge of medicament sealed with a bung and a dose dialing assembly containing a spindle configured to move the bung in an axial direction during dose delivery. There is also an inner body having a rotational counter stop, a nut threadedly engaged with the inner body and attached to a number sleeve having a proximal and a distal end. The number sleeve has a first (proximal) and a second (distal) axial position relative to the nut. The distal end of number sleeve has a sliding lock that engages the nut when the number sleeve is in the second distal position. There is a stop on the proximal end of the number sleeve that abuts the rotational counter stop on the inner body when the number sleeve is in the first axial position to prevent a user from setting a dose of medicament.

The invention also is directed to a method of ensuring a user primes the drug delivery device before setting a first dose. One method involves providing to a user a dose dial sleeve coupled with a nut threadedly engage on an inner body of a drug delivery device. The user is required to move the dose dial sleeve axially in the distal direction a specific distance to engage the nut. This pre-loads the bung in the cartridge and thus primes the drug delivery device. For disposable devices, the nut and the dose dial sleeve may engage irreversibly. However, for a reusable device it is preferred if the nut and the dose dial sleeve may disengage for resetting of the device.

Yet another method involves providing a user with a drug delivery device having a cartridge holder portion and a dose dialing portion containing a spindle, where the cartridge holder contains a cartridge containing a bung and medicament. A number sleeve (i.e. dose dial sleeve) located in the dose dialing portion is in a first axial position. The user is prevented from dialing a dose by providing a rotational stop on the number sleeve such that it engages a counter stop on an inner body when the number sleeve is in the first axial position. The user is required to move the number sleeve from the first axial position to a second axial position to disengage the stop and counter stop and to engage a sliding lock between the number sleeve and a nut attached to the inner body.

The invention also relates to a drug delivery device having a forced priming feature where the device has a cartridge holder containing a cartridge of medicament sealed with a bung and a dose dialing assembly containing a spindle configured to move the bung in an axial direction during dose delivery. The device also has a housing component, like an inner body, with a rotational counter stop. It has a nut threadedly engaged with the inner body and is in rotational engagement to a number sleeve having proximal and distal ends and having first and second axial positions. The inner body has a collar axially retained but rotationally free that is threadedly engaged with the distal end of the number sleeve such that rotation of the collar causes the number sleeve to move from the first axial position, where a user is prevented from setting a dose, to the second axial position where a dose can then be set. Movement from the first position to the second position causes the spindle to move axially preloading the bung thus priming the injection device.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
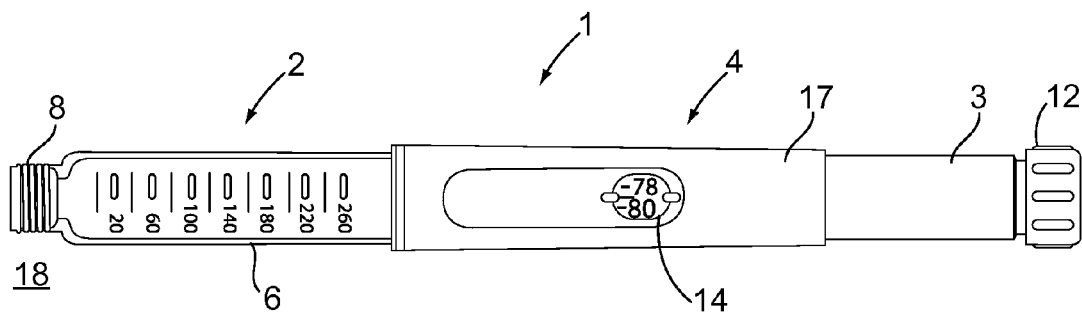
FIG. 1 illustrates the drug delivery device in accordance with the one aspect of the present invention with a cap removed and showing a cartridge holder.

The terms "drug" or "medicinal product" or "medicament", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39), des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Referring to FIG. 1, there is shown a drug delivery device 1 in accordance with an exemplary arrangement. The drug delivery device 1 comprises a housing having a first cartridge retaining part 2, and a dose setting mechanism 4. The drug delivery device may be a resettable drug delivery device (i.e., a reusable device) or alternatively a non-resettable drug delivery device (i.e., a non-reusable device). A first end of the cartridge retaining part 2 and a second end of the dose setting mechanism 4 are secured together by connecting features. For non-resettable devices, these connecting features would be permanent and non-reversible. For resettable devices, these connecting features would be releasable.

In this illustrated arrangement, the cartridge housing 2 is secured within the second end of the dose setting mechanism 4. A removable cap (not shown) is releasably retained over a second end or distal end of a cartridge retaining part or cartridge housing. The dose setting mechanism 4 comprises a dose dial grip 12 and a window or lens 14. A dose scale arrangement is viewable through the window or lens 14. To set a dose of medication contained within the drug delivery device 1, a user rotates the dose dial grip 12 such that a dialed dose will become viewable in the window or lens 14 by way of the dose scale arrangement.

FIG. 1 illustrates the medical delivery device 1 with the cover cap removed from a distal end 18 of the medical delivery device 1. This removal exposes the cartridge housing 6. Preferably, a cartridge (not shown) from which a number of doses of a medicinal product may be dispensed, is provided in the cartridge housing 6. Preferably, the cartridge contains a type of medicament that can be administered relatively often, such as once or more times a day. One such medicament is either long acting or short acting insulin or an insulin analog. The cartridge comprises a bung or stopper that is retained near a second end or a proximal end of the cartridge. The medical delivery device also comprises a driver having a spindle (not illustrated in FIG. 1, but is illustrated as items 7 and 5 in FIG. 3 and depicted in FIG. 5). As discussed above, before the device is primed, there may or may not be a gap between the end of the spindle and the cartridge bung.

The cartridge housing 6 has a distal end and a proximal end. Preferably, the distal end of the cartridge housing 6 comprises a hub 8 for attaching a removable needle assembly. However, other needle assembly connection mechanisms could also be used. If the drug delivery device 1 comprises a resettable device, the cartridge proximal end is removably connected to the dose setting mechanism 4. In one preferred embodiment, cartridge housing proximal end is removably connected to the dose setting mechanism 4 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 4 of the drug delivery device illustrated in FIG. 1 may be utilized as a reusable drug delivery device. (i.e., a drug delivery device that can be reset) Where the drug delivery device 1 comprises a reusable drug delivery device, the cartridge is removable from the cartridge housing 6. The cartridge may be removed from the device 1 without destroying the device 1 by merely having the user disconnect the dose setting mechanism 4 from the cartridge housing 6.

In use, once the cap is removed, a user can attach a suitable needle assembly to the hub 8 provided at the distal end of the cartridge housing 6. Such needle assembly may be, for example, screwed onto a distal end of the housing 6 or alternatively may be snapped onto this distal end. After use, the replaceable cap may be used to re-cover the cartridge housing 6. Preferably, the outer dimensions of the replaceable cap are similar or identical to the outer dimensions of the dose setting mechanism 4 so as to provide an impression of a unitary whole when the replaceable cap is in position covering the cartridge housing 6 when the device is not in use.

Figure 2:
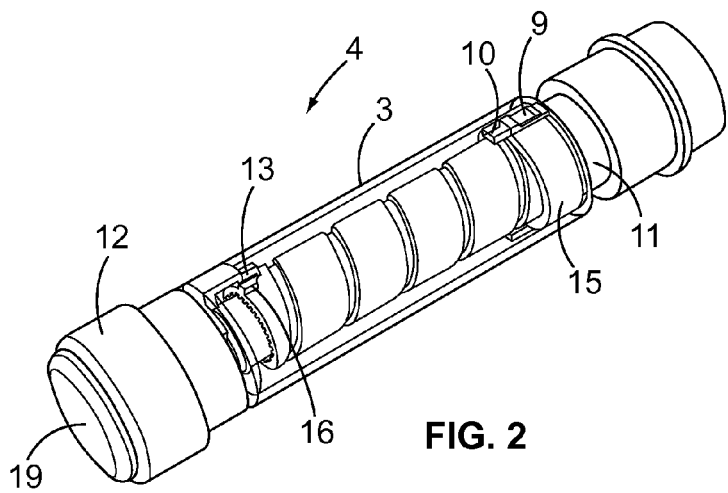
FIG. 2 is a perspective view of one embodiment of a dose setting mechanism in accordance with the invention for a drug delivery device such as the one shown in FIG. 1.
Figure 3:
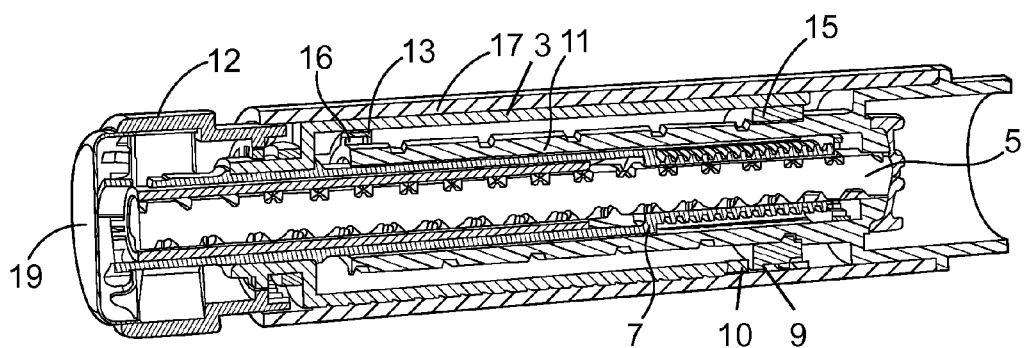
FIG. 3 illustrates a cut-away side view of the dose setting mechanism of FIG. 2.

FIGS. 2 and 3 illustrate perspective and cross sectional views of a first arrangement of a dose setting mechanism 4. Those of skill in the art will recognize that dose setting mechanism 4 may include a connection mechanism for releasably connecting to a cartridge holder, like the cartridge holder 6 illustrated in FIG. 1. However, as those of ordinary skill in the art will recognize, the dose setting mechanism may also include a permanent connection mechanism for permanently connecting to a cartridge holder.

With reference to FIGS. 2 and 3, the dose setting mechanism 4 comprises a dose dial grip 12, an outer housing 17, a driver 7, a dose dial sleeve 3, and an inner body 11 (inner housing). The dose dial sleeve is a drum-like part which is not directly in a threaded engagement with the threaded inner body 11. However, the dose dial sleeve 3 is coupled to a nut 15 that is rotationally engaged to the inner body 11. In other words, the nut 15 has an inner thread which engages the outer thread provided on the inner body 11. Further, the nut has a permanent rotational engagement with the dial sleeve such that they cannot rotate relative to each other. For this purpose, male and female (coupling) parts 9 and 10 are provided on the dose dial sleeve and the nut, respectively. In the embodiment shown in FIGS. 2 and 3, the nut 15 is located within the dose dial sleeve 3, i.e. between the dose dial sleeve and the inner body 11. The male and female parts 9 and 10 are provided by a protrusion 9 on the outer surface of the nut and an opening 10 in the dose dial sleeve which receives the protrusion 9. The opening 10 has a slit-like configuration extending in the axial direction in the embodiment of FIGS. 2 and 3 allowing a relative axial movement between dose dial sleeve 3 and nut 15.

FIGS. 2 and 3 show the dose setting mechanism in the non-primed configuration where a new cartridge of medicament has been loaded into the cartridge holder. In this position the dial (number) sleeve 3 has a relatively small amount of axial clearance relative to the nut where the dial sleeve is set back proximally from the nut. This allows the number sleeve to axially travel inward relative to the nut such that an irreversible lock is formed between male and female parts 9 and 10. This irreversible lock prevents the dial sleeve from travelling rearward relative to the nut. In pre-filled disposable injection devices the components are assembled and supplied to the user with the number sleeve in its rearward position relative to the nut. In reusable devices the dose setting mechanism is configured to allow the user to un-lock the irreversible lock as part of the procedure for removing an empty cartridge and inserting a new full cartridge. The important aspect is that the lock remains irreversible during dispensing of the medicament from the cartridge from the first dose to the last dose. In the non-primed first position of the dose dial sleeve, parts 9 and 10 are discouraged from engaging with each other by an interference fit between the two components. This can take the form of a detent or snap fit mechanism or other known male/female connection that requires a specific application of force to connect the two components. In other words, the friction between parts 9 and 10 may only be overcome by input from the user.

When the dial sleeve is in its first position as shown in FIGS. 2 and 3, i.e. axially displaced in the proximal direction away from the nut, the dial sleeve is prevented from "dialing out" in the dose setting direction by thread stop 13 and inner body stop 16. Likewise, the dial sleeve may also be prevented from "dialing in" by a stop 100 (cf. FIG. 5) between the nut and the inner body. In the embodiment shown in FIGS. 2 and 3, the inner body stop 16 is provided as a protrusion facing radially outwards near the proximal end of the inner body 11. Further, the thread stop 13 may be an integral part of the dose dial sleeve or a separate part coupled to the dose dial sleeve. The thread stop 13 and the inner body stop 16 are designed such that a rotation of the thread stop 13 and the inner body stop 16 relative to each other is prevented in the non-primed position of the device, but is allowed in its primed position.

To release the dose setting mechanism from this initial non-primed position, the user is forced or required to push dose button 19 axially, which in turn causes the dial sleeve to move axially to force parts 9 and 10 together to engage or create the lock. As an axially movement of the dose dial sleeve is transferred to the driver 7, this axially movement of the dial sleeve also causes driver 7 to act on spindle 5 moving it in the axial direction and thus pre-loads the cartridge bung. The injection device at this point is now primed. The dial sleeve is also released from the inner body stop 16 allowing it to be freely rotated during dose setting.

Figure 4:
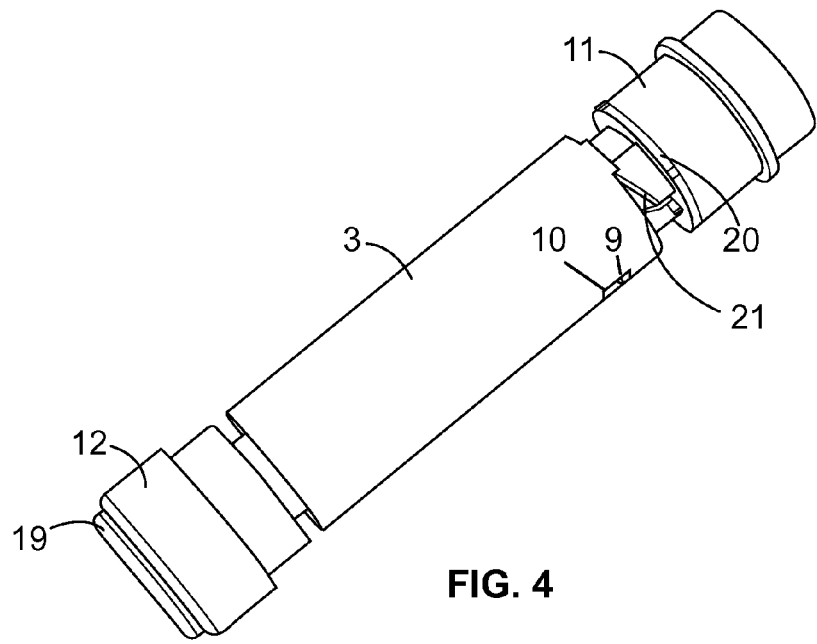
FIG. 4 is a perspective view of another embodiment of a dose setting mechanism in accordance with the invention for a drug delivery device such as the one shown in FIG. 1.
Figure 5:
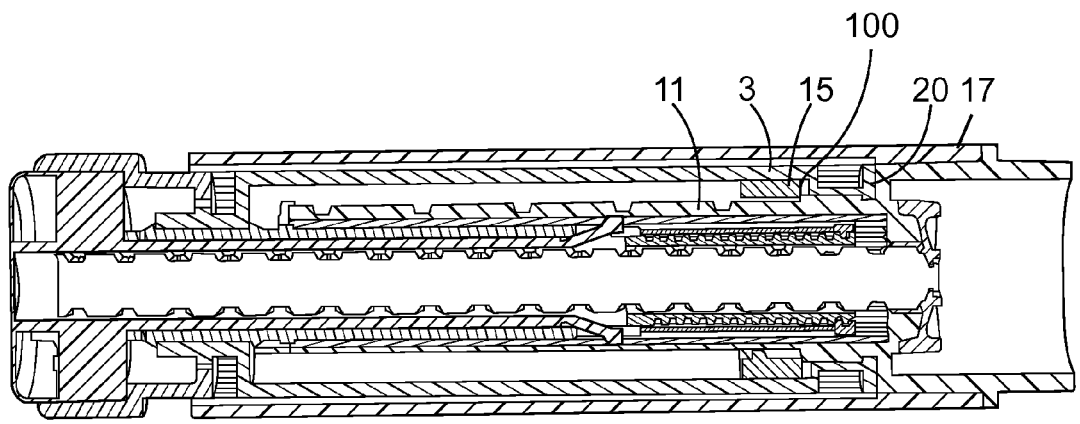
FIG. 5 illustrates a cut-away side view of the dose setting mechanism of FIG. 4.

FIGS. 4 and 5 illustrate yet another embodiment of the forced priming feature for an injection device similar to the type shown in FIG. 1. In this embodiment the forced priming feature contains a threaded collar 20, which cannot move axially relative to the inner body 11 and is also threadedly engaged with the number sleeve 3. To prime the injection device the user causes the threaded collar to rotate by either rotating the threaded collar or the cartridge holder 6 relative to body 17 (outer housing). Because the threaded collar 20 is initially threadedly engaged by threads 21 with the number sleeve, rotation of the threaded collar pulls the number sleeve forward (distal direction) via the thread engagement. During the final portion of rotation of the threaded collar the thread disengages from the number sleeve so that during dose setting the number sleeve is dialed normally without interference from the threaded collar 20.

As with the embodiment shown in FIGS. 2 and 3, this embodiment may contain stops to prevent a user from dialing out (setting a dose) prior to priming the device. A preferred design is to have the inner body contain a rotational counter stop that engages a stop on the number sleeve to prevent rotation. Movement of the number sleeve from the first non-primed position to the second primed position causes the spindle to move axially preloading the bung and thus priming the injection device. Likewise, the dose dial sleeve and the nut may have locking elements that engage when the threaded collar causes the dose dial sleeve to move axially during the priming operation.

In a preferred design, the movement of the dose dial sleeve along the rotational threaded collar may also cause the driver to rotate. This rotation of the driver may cause the spindle to advance towards the cartridge in the cartridge housing. This advancement of the spindle removes any potential initial separation between the spindle and the cartridge bung. In other words, this advancement of the spindle caused by the rotation of the dose dial sleeve and driver primes the drug delivery device.

As the dose setting mechanisms of the invention force a user to prime the device, the dose setting mechanisms described do not suffer from the drawback of possibly dispensing an incorrect dose due to the initial separation between the spindle and the cartridge bung. If a user attaches a needle to the drug delivery device before the user primes the device, then a small amount of drug may be expelled during the priming operation. Alternatively, if the user attaches the needle after priming the device or after setting the first dose, then the drug, which will be pressurized from the priming, will be expelled as the needle is connected to the drug delivery device. Accordingly, the drug amount resulting from the priming operation will be expelled before the needle is inserted into a user's skin.

In an exemplary arrangement, the drug delivery device may be designed to indicate to a user whether the device needs to be primed or does not need to be primed before dialing a dose. For instance, dose dial sleeve 3 may comprise a graphic printed on it that is displayed in the dose window 14 before the pen is primed. The graphic may display a character such as "P" or a phrase such as "Priming Needed." Other graphics are possible as well. Once a device has been primed, the graphic will no longer be displayed in the dose window.

Further, since the forced priming features of the invention contain irreversible locks or other non-return elements, the user does not have to prime the device prior to each subsequent dose. Accordingly, a dose setting mechanism in accordance with an exemplary embodiment forces a user to prime the device before the first dose is dialed, but does not force the user to prime the device for subsequent doses. However, in the event that the drug delivery device is reusable, it should be understood that a dose setting mechanism in accordance with an exemplary embodiment is designed so that the dose setting mechanism forces a user to prime the device each time a cartridge is replaced. In such a reusable device, the device is preferably designed so that a user could overcome the non-return elements. This may be accomplished, for example, by rotating the dose dial sleeve over a detent in the dialed position or possibly by pushing or pulling the dial sleeve in the proximal direction to disengage the lock. Other ways for overcoming the non-return elements are possible as well. Further, in this exemplary embodiment, it may be advantageous to force the user to do this before being able to remove the cartridge holder.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A dose setting mechanism for a drug delivery device comprising:
   a dial sleeve;
   a housing component comprising an inner body;
   a nut provided between the dial sleeve and the inner body; and
   a sliding lock on the dial sleeve;
   wherein the dial sleeve is coupled to the nut, the nut comprising an inner thread that is threadedly engaged to the inner body,
   wherein the dial sleeve moves axially with respect to the nut during priming of the drug delivery device from a first, proximal position to a second, distal position,
   wherein the sliding lock engages the nut when the dial sleeve is in the second distal position, and
   wherein the dial sleeve translates along a helical path during dose setting of the drug delivery device.

2. The dose setting mechanism of claim 1 wherein the sliding lock is irreversibly connected to the nut when the dial sleeve is in the second distal position.

3. The dose setting mechanism of claim 1 wherein the sliding lock is prevented from engaging the nut when the dial sleeve is in the first proximal position by a frictional snap fit.

4. The dose setting mechanism of claim 1 wherein the sliding lock comprises a protrusion formed on the outer surface of the nut and a slit-like opening provided in the dial sleeve and receiving the protrusion.

5. The dose setting mechanism of claim 1 wherein the nut is provided as an essentially ring-shaped element located between the dial sleeve and the housing component, which is an inner body.

6. A drug delivery device having a forced priming feature comprising
   a. a cartridge holder configured to contain a cartridge of medicament sealed with a bung;
   b. a dose setting mechanism comprising:
   a dial sleeve,
   a housing component comprising an inner body,
   a nut provided between the dial sleeve and the inner body, and
   a spindle configured to move the bung in an axial direction during dose delivery, and a rotational counterstop associated to the housing component;
   wherein the dial sleeve is coupled to the nut, the nut comprising an inner thread that is threadedly engaged to the inner body,
   wherein the dial sleeve moves axially with respect to the nut during priming of the drug delivery device from a first, proximal position to a second, distal position, and
   wherein the dial sleeve translates along a helical path during dose setting of the drug delivery device; and
   c. a stop on the dial sleeve that abuts the rotational counter stop on the housing component when the dial sleeve is in a first axial position to prevent a user from setting a dose of medicament.

7. A drug delivery device having a forced priming feature comprising
   a. a cartridge holder containing a cartridge of medicament sealed with a bung;
   b. a dose setting mechanism comprising:
   a dial sleeve,
   a housing component comprising an inner body,
   a nut provided between the dial sleeve and the inner body, and
   a spindle configured to move the bung in an axial direction during dose delivery, and a rotational counter stop associated to the housing component;
   wherein the dial sleeve is coupled to the nut, the nut comprising an inner thread that is threadedly engaged to the inner body
   wherein the dial sleeve moves axially with respect to the nut during priming of the drug delivery device from a first, proximal position to a second, distal position, and wherein the dial sleeve translates along a helical path during dose setting of the drug delivery device; and
   c. a collar threadedly engaged with the distal end of the dial sleeve such that rotation of the collar relative to the dial sleeve causes the dial sleeve to move from a first axial position where a user is prevented from setting a dose to a second axial position where a dose can then be set.

8. The drug delivery device of claim 7 where the collar is not threadedly engaged with the dial sleeve when the dial sleeve reaches the second axial position.

9. The drug delivery device of claim 6 where the spindle does not exert a force on the bung when the dial sleeve is in the first axial position.

10. The drug delivery device of claim 6 where the spindle exerts a force on the bung when the dial sleeve is in the second position.

* * * * *